United States Patent [19]

Takemoto et al.

[11] Patent Number: 5,532,407
[45] Date of Patent: Jul. 2, 1996

[54] PROCESS FOR RECOVERING L-PHENYLALANINE

[75] Inventors: Tadashi Takemoto; Takehiko Kataoka, both of Kawasaki, Japan

[73] Assignee: Ajinomoto Co., Inc., Tokyo, Japan

[21] Appl. No.: 330,185

[22] Filed: Oct. 27, 1994

[30] Foreign Application Priority Data

Dec. 13, 1993 [JP] Japan .................................. 5-311675

[51] Int. Cl.$^6$ ................................................ C07C 211/00
[52] U.S. Cl. ............................................................. 562/443
[58] Field of Search ............................................. 562/443

[56] References Cited

U.S. PATENT DOCUMENTS

| | | |
|---|---|---|
| 4,822,907 | 4/1989 | Sugiyama . |
| 5,015,386 | 5/1991 | Tanabe . |
| 5,096,590 | 3/1992 | Watanabe . |

FOREIGN PATENT DOCUMENTS

| | | |
|---|---|---|
| 0055612 | 7/1982 | European Pat. Off. . |
| 0248416 | 12/1987 | European Pat. Off. . |
| 0526854 | 2/1993 | European Pat. Off. . |

OTHER PUBLICATIONS

Database WPI, Derwent Publications, AN–74–18275V, JP–48–097812, Dec. 13, 1973.

Database WPI, Derwent Publications, AN–88–224248, JP–63–159355, Jul. 2, 1988.

*Primary Examiner*—José G. Dees
*Assistant Examiner*—Samuel Bartz
*Attorney, Agent, or Firm*—Oblon, Spivak, McClelland, Maier & Neustadt

[57] ABSTRACT

An industrial process for recovering L-phenylalanine in high yield from a side stream obtained from α-APM is disclosed. L-aspartic acid or an aqueous solution thereof is added to such a side stream when hydrolysis of the side stream is performed under acidic conditions with a mineral acid, the pH of the reaction mixture obtained by hydrolysis is then adjusted to 5 to 6 to precipitate L-phenylalanine.

6 Claims, No Drawings

PROCESS FOR RECOVERING L-PHENYLALANINE

BACKGROUND OF THE INVENTION

1. Field of the Invention

This invention relates to a process for producing α-L-aspartyl-L-phenylalanine methyl ester (hereinafter referred to as α-APM) and for recovering L-phenylalanine from the side stream generated from processes which produce α-APM.

2. Discussion of the Background

α-APM is about 200 times as sweet as sucrose and is in great demand as a dietary sweetener due to its good sweet taste and low calorie content. Various processes for producing α-APM are known, for example a process which comprises reacting N-protected L-aspartic anhydride with L-phenylalanine methyl ester (U.S. Pat. No. 3,786,039), a process which comprises reacting N-protected L-aspartic anhydride with L-phenylalanine (U.S. Pat. No. 4,173,562), and a process which comprises condensing N-benzyloxycarbonyl-L-aspartic acid and L-phenylalanine methyl ester with an enzyme (Japanese Patent Application Laid-open No. 92729-1978). However, to employ them for low cost industrial process, it is necessary to recover and reuse L-phenylalanine and L-aspartic acid from side streams obtained during the α-APM production process such as α-APM mother liquor or α-APM. HCl mother liquor, since these side streams contain a significant amount of L-phenylalanine derivatives, L-aspartic acid derivatives and β-L-aspartyl-L-phenylalanine methyl ester and α-APM. Of these, it is very important to efficiently recover L-phenylalanine, which is an expensive amino acid. Known processes for recovering L-phenylalanine from a side stream generated during a process for production of α-APM include a process disclosed in Japanese Patent Application Laid-open No. 97812-1973. The process comprises hydrolysis of a solution containing β-L-aspartyl-Lphenylalanine methyl ester in the presence of a mineral acid, adjusting the reaction solution to pH 6 for crystallization and separation of L-phenylalanine. However, the mother liquor after separation still contains a considerable amount of L-phenylalanine. Accordingly, the recovery may be further improved if the solubility of L-phenylalanine can be reduced.

The problem solved by the invention is that of establishing an industrial process to efficiently recover L-phenylalanine from side streams generated from the production of α-APM. The present inventors have intensively studied a process for efficient recovery of L-phenylalanine from side streams obtained during production of α-APM. As a result, we have found unexpectedly that the solubility of L-phenylalanine in aqueous solutions is reduced, and recovery of L-phenylalanine is improved if L-aspartic acid or an aqueous solution thereof is present when the pH of a reaction mixture obtained by hydrolysis of said side stream with a mineral acid is adjusted to 5–6, thus precipitating L-phenylalanine.

SUMMARY OF THE INVENTION

Accordingly, an object of this invention is to provide a process for recovering L-phenylalanine from production of α-APM, comprising: adding L-aspartic acid or an aqueous solution thereof to a side stream obtained from production of α-APM either before or after hydrolysis of the side stream in the presence of mineral acid, adjusting the pH of the reaction mixture obtained by hydrolysis to 5–6, and recovering precipitated L-phenylalanine.

DETAILED DESCRIPTION OF THE PREFERRED EMBODIMENTS

The typical side streams obtained from the production of α-APM include:

(i) a mother liquor obtained by crystallization and separation of α-APM from water, which is obtained by condensing N-benzyloxycarbonyl-L-aspartic anhydride and L-phenylalanine methyl ester, and by deprotecting upon reduction (U.S. Pat. No. 3,786,039);

(ii) a mother liquor obtained by separating α-APM-HCl precipitated upon condensation of N-formyl-L-aspartic acid anhydride and L-phenylalanine methyl ester, followed by treatment with methanol and hydrochloric acid at high concentration (U.S. Pat. No. 4,684,745);

(iii) a mother liquor after separation of α-APM-HCl precipitated upon esterification of α-AP with water, methanol and hydrochloric acid (U.S. Pat. No. 4,173,562).

Mineral acids used in the present invention include hydrochloric, sulfuric, phosphoric acid and the like. Hydrochloric acid is desirable considering the ease of removing salts thereof generated by adjustment of the pH after hydrolysis. During hydrolysis, the concentration of the acid is preferably 1–12N, particularly 2–6N. The amount used is desirably more than 1 molar equivalent, particularly 1.5 to 10 mol per 1 mole of amino acid and amino acid residue contained in said side stream.

The temperature for hydrolysis is desirably 60° to 120° C., especially 90°–110° C. The reaction time is not limited to any particular value because it varies depending on many factors. However, in general, too long a reaction time promotes racemization. A sufficient reaction time is generally within 20 hours.

The pH of the thus obtained hydrolyzate is adjusted with an alkali such as sodium hydroxide. L-aspartic acid or an aqueous solution thereof may be added either before or after such pH adjustment. Of course, addition may be carried out before hydrolysis without any problems. The amount of L-aspartic acid to be added is not limited. A sufficient amount is at least 10% mole based on the moles of L-aspartic acid present in the hydrolyzate.

The pH is selected from 5 to 6 from the viewpoint of the isoelectric point of L-phenylalanine. Alkali used for pH adjustment includes sodium hydroxide, potassium hydroxide, sodium carbonate, ammonia and the like. Sodium hydroxide is most preferable from the viewpoint of cost. Alkali may be directly added, however, it is desirable to add it in the form of an aqueous solution for ease of pH adjustment. The temperature for pH adjustment is not particularly limited. However, in order to precipitate L-phenylalanine dissolved after pH adjustment as much as possible, it is required to mature at a temperature not higher than 40° C. for an hour or more.

The aqueous solution of L-aspartic acid to be added can be prepared by dissolving crystalline L-aspartic acid in water. However, it is efficient to use an aqueous solution containing L-aspartic acid obtained from the production of α-APM. One embodiment is the above mother liquor obtained after crystallization and separation of L-phenylalanine. This mother liquor contains L-aspartic acid, which is generated by hydrolysis in addition to L-phenylalanine. Generally, in processes for production of α-APM, the pH of the mother liquor obtained by separating L-phenylalanine is adjusted to 2 to 3 which is the isoelectric point of L-aspartic acid, and the precipitating L-aspartic acid is separated and recovered from the mother liquor to be reused. However, there remains L-aspartic acid dissolved in this mother liquor. Usually, this mother liquor is discarded as a waste solution. Accordingly, it is efficient to use the mother liquor as the above aqueous solution. Furthermore, there exists not only L-aspartic acid but L-phenylalanine dissolved in the mother liquor. Therefore total recovery of L-phenylalanine is further improved if the mother liquor is utilized as an aqueous solution of L-aspartic acid thereby recovering L-phenylalanine in the mother liquor. This mother liquor may be directly used. However, if it is directly used, an inorganic salt may be precipitated upon increased concentration during precipitation of L-phenylalanine since there exists an inorganic salt in the mother liquor equimolar to the mineral acid used for hydrolysis. Accordingly, it is better to previously desalt the mother liquor. The desalting ratio may vary depending on various known factors so that it cannot be specified here. Generally, it is sufficient if the range is within 20 to 90%. For desalting, this mother liquor is concentrated and the precipitated inorganic salts are removed by filtration. Alternatively, a method utilizing loose reverse osmotic membrane at an appropriate pH can be employed.

L-aspartic acid used in the present invention may be easily recovered by the following method. That is, after the L-phenylalanine is separated, the pH of the filtrate is adjusted to 2 to 3, and the precipitated crystals are isolated and recovered with L-aspartic acid generated by hydrolysis.

Other features of the invention will become apparent in the course of the following descriptions of exemplary embodiments which are given for illustration of the invention and are not intended to be limiting thereof.

EXAMPLE 1

Mother liquor of α-APM·HCl (0.9 L) (concentration of HCl is 3.5N) was hydrolyzed by heating and refluxing at 110° C. for 6 hours. Analysis by an amino acid analyzer showed that the reaction solution contained 112.0 g of L-aspartic acid and 116.5 g of L-phenylalanine. After 56.0 g of L-aspartic acid was added to the reaction solution, the pH was adjusted to 5.6 with a 48% aqueous solution of caustic soda at 70° C. The pH-adjusted solution was cooled to 10° C. and stirred for 3 hours. The precipitated crystals were collected by filtration and analyzed by an amino acid analyzer. The content of L-phenylalanine was 109.3 g and the yield was 93.8% based on L-phenylalanine in the hydrolyzate. On the other hand, the concentration of L-phenylalanine in the filtered mother liquor was 0.56 g/dl.

Comparative Example 1

The reaction solution, hydrolyzed in the same manner as in Example 1, was adjusted to pH 5.6 with 48% aqueous solution of caustic soda at 70° C., and subsequently cooled to 10° C. and stirred for 3 hours. The precipitated crystals were collected by filtration and analyzed by an amino acid analyzer. The content of L-phenylalanine was 103.1 g, and the yield was 88.5% based on L-phenylalanine in the hydrolyzate. On the other hand, the concentration of L-phenylalanine in the filtered mother liquor was 1.06 g/dl.

EXAMPLE 2

35% Hydrochloric acid (85 g) was added to a mother liquor of α-APM·HCl (15.0 L) and concentrated to 0.9 L under reduced pressure. 35% hydrochloric acid (concentration of HCl, 4.0N) was added to the concentrate, then hydrolysis was carried out at 110° C. for 6 hours. Analysis by an amino acid analyzer showed that the reaction solution contained 105.8 g of L-aspartic acid and 112.6 g of L-phenylalanine. After 105.8 g of L-aspartic acid was added to the reaction solution, the pH was adjusted to 5.6 with a 48% aqueous solution of caustic soda at 50° C. The pH-adjusted solution was cooled to 10° C. and stirred for 3 hours. The precipitated crystals were collected by filtration and analyzed by an amino acid analyzer. The content of L-phenylalanine was 102.8 g, and the yield was 91.3% based on L-phenylalanine in the hydrolyzate.

Comparative Example 2

L-Phenylalanine was obtained in the same manner as in Example 2, except that no amino acid was added to the hydrolyzate. The amount of L-phenylalanine otained was 96.3 g, and the yield was 85.5% based on L-phenylalanine in the hydrolyzate.

EXAMPLE 3

Mother liquor of α-APM·HCl (118 L) was hydrolyzed and adjusted to pH 5.6. The precipitated L-phenylalanine was removed by filtration. The resulting mother liquor was adjusted to pH 2.8, and the precipitated L-aspartic acid was removed by filtration. The resulting mother liquor (190 L) (concentration of ingredients: L-phenylalanine, 0.9 g/dl; L-aspartic acid, 1.7 g/dl; sodium chloride, 25.7 g/dl) was adjusted to pH 5.1 with 48% caustic soda. After dilution by 1.4 fold with water, the product was desalted and concentrated using loose reverse osmotic membrane at 30° C. A loose reverse osmotic membrane NTR-7250 (manufactured by NITTO DENKO CORPORATION), membrane of 1.8 m$^2$ area was used. The above mother liquor was passed through the loose reverse osmotic membrane under pressure of 27 kgf/cm$^2$ to concentrate 2.2 fold times, simultaneously removing 50% of the sodium chloride in the mother liquor, transferring into the permeated solution. Subsequently, water was added to the concentrate to dilute if 2.1 fold, and again concentrated using loose reverse osmotic membrane under pressure of 27 kgf/cm$^2$ (concentration ratio, 2.6 fold), and finally, 100 L of concentrated and desalted solution (content: L-phenylalanine, 1.3 g/dl; L-aspartic acid, 3.1 g/dl; sodium chloride, 11.9 g/dl) was obtained by removing 75% of the sodium chloride contained in the original mother liquor, transferring into the permeated solution.

To the mother liquor of α-APM·HCl (186 L, same as that used in Example 1; containing 25.5 kg of L-phenylalanine, 24.2 kg of L-aspartic acid; HCl concentration, 3.5N) was added 100 L of the above concentrated and desalted solution containing 3.1 kg of L-aspartic acid and 1.3 kg of L-phenylalanine. The resulting solution was concentrated under reduced pressure to obtain 177 L of the concentrate. The concentrate was heated and refluxed at 110° C. for 5 hours for hydrolysis. The reaction solution was adjusted to pH 7.0 with 48% caustic soda at 70° C., then cooled to 10° C. and stirred at the same temperature for 3 hours. The precipitated crystals were collected by filtration and analyzed by an amino acid analyzer. The content of L-phenylalanine was 24.3 kg, and the yield was 96.4% based on L-phenylalanine in the mother liquor of APM·HCl.

Comparative Example 3

Water (100 L) was added to the mother liquor of α-APM·HCl (186 L), concentrated under reduced pressure to obtain concentrate (177 L). The concentrate was hydrolyzed by heating and refluxing at 110° C. for 5 hours. The reaction solution was adjusted to pH 5.6 with 48% caustic soda at 70° C., then cooled to 10° C. and stirred at that temperature for 3 hours. The precipitated crystals were collected by filtration and analyzed by an amino acid analyzer. The content of L-phenylalanine was 21.6 kg, yield was 85.7% based on L-phenylalanine in the mother liquor of α-APM·HCl.

EXAMPLE 4

After an α-APM·HCl mother liquor (118 L) was hydrolyzed, the pH was adjusted to 5.6 and the precipitated L-phenylalanine was removed by filtration. Further, the pH of the resulting mother liquor was adjusted to 2.8 and the precipitated L-aspartic acid was removed by filtration. The resulting mother liquor (190 L) (content: L-phenylalanine, 0.9 g/dl; L-aspartic acid, 1.7 g/dl; sodium chloride, 25.7 g/dl) was adjusted to pH 5.1 with 48% caustic soda. The solution was concentrated to 110 L under reduced pressure, then stirred at 60° C. for an hour. The precipitated crystals of sodium chloride were removed by filtration. The filtrate (88 L, containing 3.2 kg of L-aspartic acid and 1.7 kg of L-phenylalanine) was added to α-APM·HCl mother liquor (186 L, containing 24.2 kg of L-aspartic acid and 25.2 kg of L-phenylalanine) and concentrated to 177 L under reduced pressure. The concentrate was hydrolyzed by heating and refluxing at 110° C. for 5 hours, then the pH was adjusted to 5.6 with 48% caustic soda at 60° C. Subsequently, the solution was cooled to 10° C. and stirred at that temperature for 3 hours. The precipitated crystals were collected by filtration and analyzed by an amino acid analyzer. The content of Lphenylalanine was 24.9 kg and the yield was 98.8% based on Lphenylalanine in the α-APM·HCl mother liquor.

Obviously, numerous modifications and variations of the present invention are possible in light of the above teachings. It is therefore to be understood that within the scope of the appended claims, the invention may be practiced otehrwise than as specifically described herein.

What is claimed as new and desired to be secured by Letters Patent of the United States is:

1. A process for recovering L-phenylalanine from production of α-APM, comprising: adding L-aspartic acid or an aqueous solution thereof directly to a side stream obtained from production of α-APM either before or after hydrolysis of the side stream in the presence of a mineral acid, adjusting the pH of the reaction mixture obtained by hydrolysis to 5–6 and recovering precipitated L-phenylalanine.

2. A process according to claim 1, wherein the aqueous solution of L-aspartic acid to be added is a mother liquor obtained after separation of said precipitated L-phenylalanine or a solution with reduced mineral salt content upon desalting of the mother liquor.

3. A process according to claim 1, wherein the aqueous solution of L-aspartic acid to be added is a mother liquor obtained by separating said precipitated L-phenylalanine, adjusting the pH of said mother liquor to 2–3 followed by separating the precipitated L-aspartic acid, or a solution with reduced mineral salt upon desalting of the mother liquor.

4. A process according to claim 1 wherein the mineral acid is hydrochloric acid.

5. A process according to claim 2, wherein loose reverse osmotic membrane is employed for desalting.

6. A process according to claim 2, wherein said desalting operation comprises precipitating and filtering mineral salt after concentration.

\* \* \* \* \*